US005427787A

United States Patent [19]

Yang et al.

[11] Patent Number: 5,427,787
[45] Date of Patent: Jun. 27, 1995

[54] ANTI-ULTRAVIOLET BIOCIDAL COMPOSITION

[75] Inventors: Chien-Chun Yang, Hsin-Chu; I-Horng Pan, Tainan; Mei-Hueih Chen, Hsinshu; Suey-Sheng Kao, Taipei; Yeong-Sheng Tsai, Hsien, all of Taiwan

[73] Assignee: Industrial Technology Research Institute, Hsinchu, Taiwan

[21] Appl. No.: 153,355

[22] Filed: Nov. 15, 1993

[51] Int. Cl.[6] ..................... A01N 63/00; A01N 59/16; A01N 43/64; C12N 1/20

[52] U.S. Cl. .............................. 424/93.461; 424/617; 435/252.3; 435/832; 514/359

[58] Field of Search ........................... 424/617, 93.461; 514/359; 435/832, 252.3

[56] References Cited

U.S. PATENT DOCUMENTS

| | | | |
|---|---|---|---|
| 3,541,203 | 11/1970 | Fogle et al. | 424/17 |
| 3,984,541 | 10/1976 | Letchworth et al. | 424/174 |
| 4,948,586 | 8/1990 | Bohm et al. | 424/406 |
| 5,322,853 | 6/1994 | Ackermann et al. | 514/359 |

FOREIGN PATENT DOCUMENTS

| | | |
|---|---|---|
| 1508020 | 12/1967 | France . |
| 2139625 | 11/1972 | Germany . |
| 3335360 | 3/1984 | Germany . |
| 61-60691 | 3/1986 | Japan . |
| 61-148106 | 7/1986 | Japan . |

OTHER PUBLICATIONS

Gabriele, P. D. et al., "J. Coat Technol," vol. 56(712), May 1984, pp. 33–48.

R. L. Dunkle et al., "Starch–Encapsulated *Bacillus thuringiensis*: A Potential New Method for Increasing Environmental Stability of Entomopathogens" Environmental Entomology/vol. 17 No. 1/1988/pp. 120∼126.

*Primary Examiner*—Irene Marx

*Assistant Examiner*—Kristin Larson

*Attorney, Agent, or Firm*—W. Wayne Liauh

[57] ABSTRACT

A biocidal formulation with improved resistance to ultraviolet rays comprising: (a) an appropriate biocide which is *Bacillus thuringiensis;* (b) an anti-ultraviolet agent selected from the group consisting of 2-(2-H-benzotriazole-2-yl)-phenol and their derivatives represented by the following formula:

wherein $R_1$ and $R_2$ are independently selected from the group consisting of alkyl, aryl, and alkylaryl groups; (c) pre-gelatinized starch; and (d) natural starch, the biocide, the anti-ultraviolet agent, the pre-gelatinized starch and the natural starch are mixed then baked at 60°–90° C. to form the biocidal formulation.

6 Claims, No Drawings

ANTI-ULTRAVIOLET BIOCIDAL COMPOSITION

FIELD OF THE INVENTION

This invention relates to a biocidal formulation with improved resistance against degradation upon exposure to ultraviolet rays. More particularly, this invention relates to a biocidal formulation which comprises at least one biocide, at least one anti*ultraviolet agent, and, optionally, starch.

BACKGROUND OF THIS INVENTION

The conventional way in the prevention of agricultural pests always involves the use of large amounts of chemical pesticides. However, long term usage of chemical pesticides may cause pests to attain resistance to the pesticides. Large dosages of pesticides also cause the problems of residuals of pesticides which could cause pesticidal pollution to the environment. Since chemical pesticides are potentially dangerous to human beings and the environment, the amounts of chemical pesticides should preferably be reduced whenever practicable and their applications limited. It is also preferred that the biocides to be used can effectively and selectively kill pests and which can be degraded in the environment. The quantity and types of biocides should be judiciously selected so that they will not harm human beings or crops.

One of the disadvantages of biocides is that most biocides cannot resist high temperatures. Preparations of biocidal formulation at high temperature may destroy biocides or reduce the activity thereof. Therefore, conventionally, the preparation of biocidal formulation must be processed at low temperature in order to protect biocides and maintain their activities.

R. L. Dunkle et at discloses a method for the preparation of starch-encapsulated *Bacillus thuringiensis* in *Environment Entomology* (vol. 17, 120–126, 1988). This reference teaches the preparation of starch-encapsulated biocide as follows. Refined corn oil (2 g) was mixed with pre-gelatinized starch powder (25 g), Chilled distilled water (60 ml, 2° C.) containing a suspension of *Bacillus thuringiensis* spores and crystals at a desired concentration was stirred into the starch-oil mixture to form a gelatinous mass. The mixture was allowed to stand for 30 minutes at room temperature to produce a rubbery but non-sticky mass which was processed in a blender with the addition of 25 g of starch powder to produce small particles. After being air dried for 24 hours at room temperature, the particles were sieved into various mesh sizes. This process was applied in order to avoid the reduction of the activity of biocide due to heat or high temperature. However, this process is cumbersome and cannot be performed as a continuous process.

Another disadvantage of the conventional biocides is that most biocides can be easily destroyed upon exposure to sunlight. The ultraviolet rays of the sunlight is specifically harmful to biocides. Thus biocides must be applied frequently and in large quantities in order to supplement the loss due to degradation and thus to effectively kill pests. Since large amounts of biocides, i.e., much larger than the optimum required of biocides, are required to achieve the desired biocidal activity, the conventional method for the application of biocides is not economical; it also can cause health and environmental concerns.

Several researchers have studied the use of anti-ultraviolet agent in order to protect biocides against ultraviolet degradation. R. L. Dunkle et al. discloses the application of 4-aminoazobenzene as an anti-ultraviolet agent in *Environmental Entomology* (Vol. 17, 120–126, 1988). With their formulation, after the biocide is exposed to ultraviolet rays for 24 hours, the mortality of pests is only 13–63% on the seventh day. In U.S. Pat. No. 3,541,203, M. V. Ogle et al. disclose a method which employs carbon black and metal powder as a protective agent in the biocidal formulation. The mortality of pests reaches the maximum on the fifth day. However, in their tests, they did not expose their biocidal formulation to ultraviolet ray; therefore, it cannot be said that their protective agents are effective as anti-ultraviolet agent. In U.S. Pat. No. 4,918,586, H. A. Bohm et al. disclose a method which employs benzophenone, para-aminobenzoic acid, benzyl, methyl orange, methyl green, malachite green, brilliant green, methyl blue, FDC green, FDC red and acridine yellow as anti-ultraviolet agents. However, with their formulations, the mortality of pest was tested to be in the range of 30.7% and 71.43%.

SUMMARY OF THE PRESENT INVENTION

Having discussed the importance and desirability for a biocidal composition to possess ultraviolet resistance, and the inadequacy of prior art biocidal formulations to provide such capability, the primary object of the present invention is, therefore, to develop a biocidal formulation which provides excellent biocidal activity even after exposure to ultraviolet light.

This invention relates to the preparation of a biocidal formulation which contains at least one biocide, at least one anti-ultraviolet agent, starch and water. The ingredients of the biocidal formulation are processed at 60°–90° C., dried for 2–15 minutes and crushed.

The present invention discloses a biocidal formulation which comprises at least one biocide and at least one anti-ultraviolet agent. The biocidal formulation of the present invention may optionally contain starch. After many years of dedicated research, the co-inventors of the present invention found that titanium dioxide and the derivatives of 2-(2-H-benzotriazole-2-yl) phenol can serve as excellent anti-ultraviolet agents, which, when added to a biocidal formulation, can effectively protect biocide against degradation upon exposure to ultraviolet light.

The derivatives of 2-(2-H-benzotriazole-2-yl) phenol disclosed in the present invention are represented by the following formula:

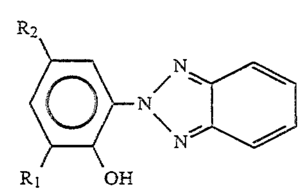

wherein $R_1$ and $R_2$ are independently selected from the group consisting of alkyl, aryl, and alkylaryl groups.

Preferred species of the derivatives of 2-(2-H-benzotriazole-2-yl) phenol include the following compounds represented by the following formulas:

Compound I (Tradename "TINUVIN TM 234"):

-continued

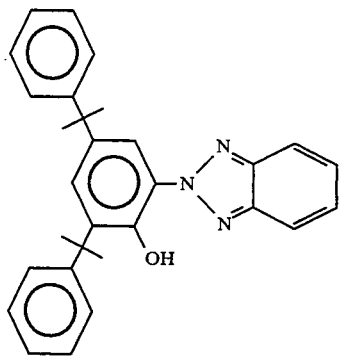

Compound II (Tradename "TINUVIN ™ 350")

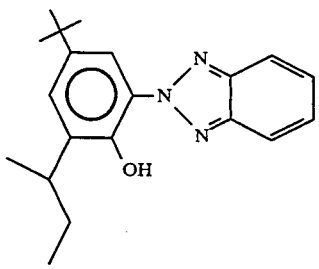

Compound III (Tradename "TINUVIN ™ P")

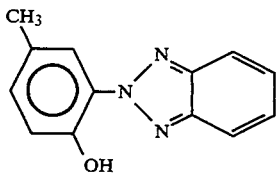

DESCRIPTION OF THE PREFERRED EMBODIMENT

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

Preparation of the *Bacillus thuringiensis* Culture

*Bacillus thuringiensis* was added into a 500 ml Hinton flask which contained 75 ml of an appropriate culture medium. The flask was stirred at 200 rpm and 30° C. for 72 hours. After the culture preparation, the flask was sampled and found to contain 2-3$\times 10^{-3}$ spores/ml. The spores were freezed to dry.

EXAMPLE 1

Pre-gelatinized starch (16.25 g), natural starch (81.3 g), *Bacillus thuringiensis* (1.0 g), and water (53.6 g) were blended to form a homogeneous mass. The mass was dried at room temperature and crushed into flakes. The flakes were sieved and various sizes of the flakes containing the biocidal formulation were obtained which were exposed to 310 nm ultraviolet rays for 24 hours. The results of mortality tests conducted on 3-instar moth larva are shown in Table 1.

Table 1 shows that the size of biocidal formulation influenced the anti-ultraviolet ability of the formulation. When the size of the formulation was small, the anti-ultraviolet ability was inefficient. R. L. Dunkle used larger flake size of his biocidal formulation to protect biocides.

TABLE 1

| Flake Size | Exposed to UV | number of moth larva tested | number of moth larva died | Mortality of moth larva |
|---|---|---|---|---|
| >10 mesh | No | 130 | 130 | 100 |
| | Yes | 130 | 80 | 62 |
| 10-25 mesh | No | 130 | 130 | 100 |
| | Yes | 130 | 59 | 45 |
| 25-40 mesh | No | 130 | 130 | 100 |
| | Yes | 130 | 26 | 20 |
| <40 mesh | No | 130 | 130 | 100 |
| | Yes | 130 | 17 | 12 |

EXAMPLE 2

Pre-gelatinized starch (312 g), natural starch (1650 g), *Bacillus thuringiensis* (19.2 g), and water (1030 g) were blended to form a mass. The mass was separated to equal portions. Each portion of the mass had 150 g of dried weight which was equivalent to 232 g of wet weight. Various anti-ultraviolet agents (at 6 g and 18 g, respectively) were blended with each portion of the mass, respectively. The mixture was rolled and pressed by a hot roller at 60°-90° C. for 2.5-5 minutes. Then the product was crushed to obtain various sizes of biocidal formulations in the form of flakes. After the biocidal formulation of the present invention was exposed to 310 nm ultraviolet rays for 24 hours, the mortality of 3-instar moth larva was studied with the results shown in Tables 2(a)-(d). Table 2(e) contains mortality data for the same biocidal formulation that does not contain anti-ultraviolet agents.

EXAMPLE 3

Pre-gelatinized starch (163 g), natural starch (921 g), *Bacillus thuringiensis* (20 g) and water (536 g) were blended to form a mass. The mass was divided into several equal portions. Each portion of the mass had 150 g of dried weight which was equivalent to 222 g of wet weight. Various anti-ultraviolet agents at various concentrations (2 g-16 g) were blended with each portion, respectively. The mixture was rolled and pressed by a hot roller at 60°-90° C. for 2.5-5 minutes. Then the product was crushed into flakes of various sizes. After the biocidal formulation of the present invention was exposed to 310 nm ultraviolet rays for 16 hours, the mortality of 3-instar moth larva was studied with the results shown in Tables 3(a)-(c). Table 3(d) contains mortality data for the same biocidal formulation that does not contain anti-ultraviolet agents. Tables 3(a)-(d) show that the biocidal formulations were effective in protecting biocides against ultraviolet degradation even at low concentrations of the anti-ultraviolet agents used in the present invention. Without the anti-ultraviolet agents, the biocides lost essentially all their activities after exposure to ultraviolet ray.

In Table 3, two various dosages of the biocidal formulations were used; they are described below:

Dosage B: 0.06 g of the biocidal formulation prepared above was exposed to 310 nm UV (0.85 $mW/cm^2$ strength) for 16 hours. The biocidal formulation was dispersed in 10 ml water. Then 2 ml of the aqueous solution was sprayed on both sides of cabbage leaves to test the mortality of moth larva.

Dosage A: 0.1 g of the biocidal formulation prepared above was exposed to 310 nm UV for 16 hours. The biocidal formulation was dispersed in 10 ml water. Then 2 ml of the aqueous solution was sprayed on both sides of cabbage leaves to test the mortality of mortality of moth larva.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 2(a)

| Anti-ultraviolet agent | Concentration | Size | Exposed to UV ray | mortality of moth larva 1 day | 2 days | 3 days |
|---|---|---|---|---|---|---|
| $TiO_2$ | 3.85% | 25–40 mesh | No | 20 | 98 | 100 |
|  |  |  | Yes | 0 | 100 | 100 |
|  |  | <40 mesh | No | 30 | 100 | 100 |
|  |  |  | Yes | 2 | 82 | 100 |
|  | 10.7% | 25–40 mesh | No | 6 | 96 | 100 |
|  |  |  | Yes | 12 | 100 | 100 |
|  |  | <40 mesh | No | 6 | 100 | 100 |
|  |  |  | Yes | 0 | 100 | 100 |

TABLE 2(b)

| Anti-ultraviolet agent | Concentration | Size | Exposed to UV ray | mortality of moth larva 1 day | 2 days | 3 days |
|---|---|---|---|---|---|---|
| (2-(2H-benzotriazol-2-yl)-4,6-bis(1-methyl-1-phenylethyl)phenol) | 3.85% | 25–40 mesh | No | 8 | 98 | 100 |
|  |  |  | Yes | 4 | 88 | 96 |
|  |  | <40 mesh | No | 10 | 98 | 100 |
|  |  |  | Yes |  |  |  |
|  | 10.7% | 25–40 mesh | No | 50 | 98 | 100 |
|  |  |  | Yes | 22 | 84 | 100 |
|  |  | <40 mesh | No | 60 | 96 | 98 |
|  |  |  | Yes | 28 | 94 | 100 |

TABLE 2(c)

| Anti-ultraviolet agent | Concentration | Size | Exposed to UV ray | mortality of moth larva 1 day | 2 days | 3 days |
|---|---|---|---|---|---|---|
| (benzotriazole phenol derivative) | 3.85% | 25–40 mesh | No | 56 | 98 | 100 |
|  |  |  | Yes | 18 | 80 | 98 |
|  |  | <40 mesh | No | 52 | 100 | 100 |
|  |  |  | Yes | 34 | 96 | 100 |
|  | 10.7% | 25–40 mesh | No | 64 | 100 | 100 |
|  |  |  | Yes | 32 | 84 | 100 |
|  |  | <40 mesh | No | 50 | 94 | 100 |
|  |  |  | Yes | 22 | 98 | 100 |

TABLE 2(d)

| Anti-ultraviolet agent | Concentration | Size | Exposed to UV ray | mortality of moth larva | | |
|---|---|---|---|---|---|---|
| | | | | 1 day | 2 days | 3 days |
| 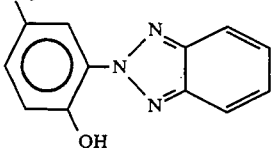 | 3.85% | 25–40 mesh | No | 20 | 100 | 100 |
| | | | Yes | 0 | 50 | 78 |
| | | <40 mesh | No | 10 | 100 | 100 |
| | | | Yes | 0 | 28 | 52 |
| | 10.7% | 25–40 mesh | No | 18 | 100 | 100 |
| | | | Yes | 2 | 80 | 96 |
| | | <40 mesh | No | 12 | 100 | 100 |
| | | | Yes | 2 | 64 | 86 |

TABLE 2(e)

| Anti-ultraviolet agent | Comparative Experiment* | |
|---|---|---|
| | Exposed to UV ray | Mortality after 3 days |
| None | No | 100 |
| | Yes | 0 |

TABLE 3(a)

| Anti-ultraviolet agent | Concentration | Size | Exposed to UV ray | mortality of moth larva | |
|---|---|---|---|---|---|
| | | | | Dosage B | Dosage A |
| TiO₂ | 1.32% | 25–40 mesh | No | 97 | |
| | | | Yes | 93 | |
| | | <40 mesh | No | 94 | |
| | | | Yes | 77 | |
| | 2.60% | 25–40 mesh | No | 98 | |
| | | | Yes | 99 | |
| | | <40 mesh | No | 92 | |
| | | | Yes | 89 | |
| | 3.85% | 25–40 mesh | No | 99 | |
| | | | Yes | 96 | |
| | | <40 mesh | No | 98 | |
| | | | Yes | 91 | |

TABLE 3(b)

| Anti-ultraviolet agent | Concentration | Size | Exposed to UV ray | mortality of moth larva | |
|---|---|---|---|---|---|
| | | | | Dosage B | Dosage A |
| 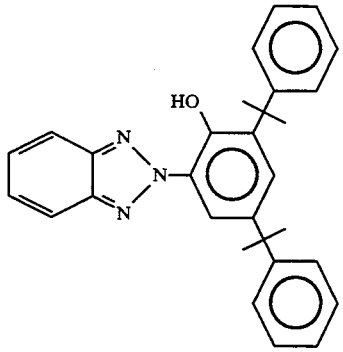 | 1.32% | 25–40 mesh | No | 97 | 100 |
| | | | Yes | 36 | 97 |
| | | <40 mesh | No | 95 | 97 |
| | | | Yes | 20 | 68 |
| | 2.60% | 25–40 mesh | No | 100 | 100 |
| | | | Yes | 72 | 100 |
| | | <40 mesh | No | 99 | 98 |
| | | | Yes | 44 | 77 |
| | 3.85% | 25–40 mesh | No | 97 | 95 |
| | | | Yes | 77 | 88 |
| | | <40 mesh | No | 96 | 100 |
| | | | Yes | 69 | 97 |

TABLE 3(c)

| Anti-ultraviolet agent | Concentration | Size | Exposed to UV ray | mortality of moth larva Dosage B | Dosage A |
|---|---|---|---|---|---|
| 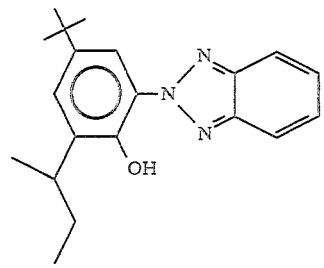 | 1.32% | 25–40 mesh | No | 98 | 100 |
| | | | Yes | 82 | 86 |
| | | <40 mesh | No | 100 | 100 |
| | | | Yes | 62 | 64 |
| | 2.60% | 25–40 mesh | No | 94 | 100 |
| | | | Yes | 64 | 95 |
| | | <40 mesh | No | 92 | 46 |
| | | | Yes | 100 | 76 |
| | 3.85% | 25–40 mesh | No | 98 | 100 |
| | | | Yes | 80 | 96 |
| | | <40 mesh | No | 100 | 100 |
| | | | Yes | 62 | 75 |

TABLE 3(d)

| | Comparative Experiment | | |
|---|---|---|---|
| | Exposed to | mortality of moth larva | |
| Size | UV ray | Dosage B | Dosage A |
| <40 mesh | No | 90 | 99 |
| | Yes | 10 | 10 |

What is claimed is:

1. A biocidal formulation with resistance to ultraviolet rays comprising:

(a) *Bacillus thuringiensis;*

(b) an anti-ultraviolet agent selected flora the group consisting of 2-(2-H-benzotriazole-2-yl)-phenol and derivatives thereof represented by the formula:

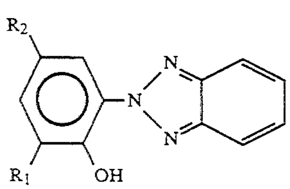

wherein $R_1$ and $R_2$ are independently selected from the group consisting of alkyl, aryl, and alkylaryl groups;

(c) pre-gelatinized starch; and (d) natural starch;

wherein said biocide, said anti-ultraviolet agent, said pre-gelatinized starch and said natural starch are mixed then baked at 60°–90° C. to form said biocidal formulation.

2. The biocidal formulation in accordance with claim 1 wherein said anti-ultraviolet agent is a 2-(2-H-benzotriazole-2-yl)-phenol derivative represented by the formula:

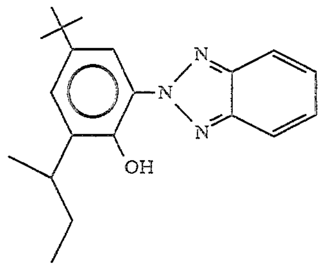

3. The biocidal formulation in accordance with claim 1 wherein said anti-ultraviolet agent is a 2-(2-H-benzotriazo-2-yl)-phenol derivative represented by the formula:

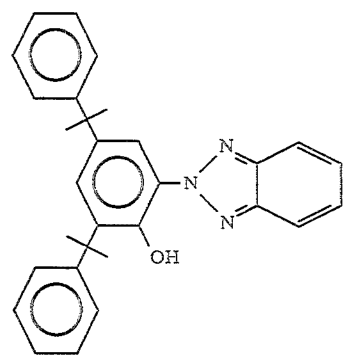

4. The biocidal formulation in accordance with claim 1 wherein said anti-ultraviolet agent is a 2-(2H-benzotriazo-2-yl)-phenol derivative represented by the formula:

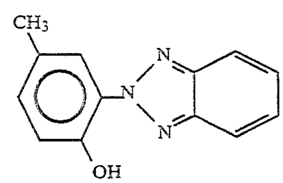

5. The biocidal formulation in accordance with claim 1 wherein said anti-ultraviolet agent constitutes 1–15% based on dried weight of said biocidal formulation.

6. The biocidal formulation in accordance with claim 5 wherein said anti-ultraviolet agent constitutes 1–10% based on dried weight of said biocidal formulation.

* * * * *